(12) United States Patent
Danielsson et al.

(10) Patent No.: US 6,778,629 B1
(45) Date of Patent: Aug. 17, 2004

(54) COMPUTED TOMOGRAPHY METHOD INVOLVING A HELICAL RELATIVE MOTION

(75) Inventors: Per-Erik Danielsson, Linkoping (SE); Henrik Turbell, Linkoping (SE)

(73) Assignee: Koninklijke Philips Electronics N.V., Eindhoven (NL)

(*) Notice: Subject to any disclaimer, the term of this patent is extended or adjusted under 35 U.S.C. 154(b) by 0 days.

(21) Appl. No.: 09/663,634

(22) Filed: Sep. 18, 2000

(30) Foreign Application Priority Data

Sep. 18, 1999 (DE) .......................................... 199 44 701

(51) Int. Cl.⁷ ................................................ A61B 6/03
(52) U.S. Cl. ............................. 378/15; 378/4; 378/901
(58) Field of Search .............................. 378/4, 15, 901

(56) References Cited

U.S. PATENT DOCUMENTS

| | | | | |
|---|---|---|---|---|
| 5,796,803 A | * | 8/1998 | Flohr et al. .................... | 378/15 |
| 5,881,122 A | | 3/1999 | Crawford et al. .............. | 378/4 |
| 6,285,733 B1 | * | 9/2001 | Proksa et al. .................. | 378/15 |

FOREIGN PATENT DOCUMENTS

| | | | | |
|---|---|---|---|---|
| WO | WO 98/30980 | * | 7/1998 | ........... G06T/11/00 |
| WO | WO 98/36885 | * | 7/1999 | ........... G06T/11/00 |
| WO | WO9936885 | | 7/1999 | ........... G06T/11/00 |

OTHER PUBLICATIONS

Turbell et al., "An improved PI–method for reconstruction from helical cone–beam projections," Nuclear Science Symposium/Medical Imaging Conference, 'Online! 28/10/99, Seiten 865–868 im Conf. Record, vol. 2.

Danielsson et al., "Towards Exact 3D–Reconstruction for Helical Cone–Beam Scanning of Long Objects. Anew Detector Arrangement and a New Completemess Condition—Poster," int. Meeting On Fully Three–dimensional Image Reconstruction In Radiology And Nuclear Medicine, 27/6/97.

* cited by examiner

Primary Examiner—Robert H. Kim
Assistant Examiner—C Kao

(57) ABSTRACT

The invention relates to a computed tomography method in which a conical radiation beam traverses an examination zone during a helical relative motion between the radiation beam and the examination zone. The reconstruction is performed by means of filtered backprojection, the filtering operations involving measured values resulting from different projections of voxels from at least approximately the same surface within the examination zone.

7 Claims, 4 Drawing Sheets

COMPUTED TOMOGRAPHY METHOD INVOLVING A HELICAL RELATIVE MOTION

BACKGROUND OF THE INVENTION

1. Field of the Invention

The invention relates to a computed tomography method which includes the following steps:

generating a conical radiation beam which emanates from a radiation source and traverses an examination zone or an object situated therein, generating a relative motion in the form of a helix, comprising a rotation about an axis of rotation and a displacement parallel to the axis of rotation, between the radiation source on the one side and the examination zone or the object on the other side, acquiring, during the relative motion and using a detector unit, measured values which are dependent on the intensity in the radiation beam to the other side of the examination zone, rebinning the measured values so as to form a number of groups of measured data, filtering the measured data of the groups formed by rebinning, which filtering involves filtering operations performed on different sub-groups of measured data, reconstructing the absorption in voxels of the examination zone by backprojection of the filtered measured data of different groups.

2. Description of Related Art

A computed tomography method of this kind is known from PCT/IB 99/00027 (PHQ 98-020). Rebinning produces groups of measured data which are associated with rays which would occur if a flat, rectangular detector in a plane containing the axis of rotation were to detect the measured data of a radiation source extending along a helix arc and emitting fan beams perpendicularly to the detector plane and parallel to the axis of rotation. All measured data belonging to parallel fan beams then form a group which is composed of a number of sub-groups. Each sub-group comprises the measured data which are subjected to a common filtering operation and are associated with a horizontal row of the (virtual) detector. Despite an attractive quality of the CT image produced from the filtered measured data by backprojection, such an image may still contain image artefacts, particularly if the conical radiation beam has a large angle of aperture in the direction perpendicular to the axis of rotation and parallel thereto.

OBJECTS AND SUMMARY OF THE INVENTION

It is an object of the present invention to enhance the image quality further in a method of the kind set forth. This object is achieved in that the subdivision into sub-groups is such that the measured data of different sub-groups result from different projections of voxels from at least approximately the same surface within the examination zone.

Each group of measured data comprises the projection of all voxels each time present in the beam path in a given projection direction. A part of these voxels belongs to each sub-group of measured data subjected to a (common) filtering operation. According to the known method the collection of voxels whereto the measured data subjected to a common filtering operation belong changes from one projection to another. The invention is based on the insight that the image artefacts involved in the known method result from such a continuously changing collection. Therefore, according to the invention the filtering operations in the various groups of measured data or for the different projections always involve those measured data which result, at least approximately, from the projection of the same voxels in the object to be examined. The image quality is thus enhanced.

The principle on which the invention is based, i.e. carrying out the filtering operation in such a manner that the filtering operations involve the measured data resulting from different projections of each time the same voxels, is not only valid for the method set forth in the preamble. It can be very advantageously used, however, in its version and in which a rebinning operation is performed so as to form groups of measured data which are associated with rays situated in planes parallel to one another and parallel to the axis of rotation.

When the surface is projected from a different direction, the projection on the detector unit usually will no longer describe a line but rather an elongated surface. Even though only one-dimensional filtering takes place along a (curved) line approximating said surface in a further embodiment, image artefacts are suppressed to a high degree. However, a one-dimensional filtering operation is performed along a straight line which approximates said surface, the image quality thus also being enhanced.

In the preferred embodiment the radiation source and the detector unit describe an angle of exactly 180° (viewed from the relevant voxel) around each voxel from its entry into the conical radiation beam until its exit therefrom.

The best image quality can be achieved when first a three-dimensional reconstruction of the absorption distribution in the examination zone is performed and subsequently the absorption distribution within arbitrary two-dimensional layers is extracted therefrom. In another embodiment, however, first a two-dimensional reconstruction takes place in a flat layer which approximates the surface on which the voxels subjected to a common filtering operation are situated. The image quality, however, is not as good as that of the image of the relevant layer when derived from a three-dimensional reconstruction. The method can also be repeated for a plurality of (two-dimensional) layers which are in mutation relative to the axis of rotation and wherefrom a three-dimensional zone can be reconstructed (with a lower image quality). This is known per se from WO 98/448847.

A computed tomograph is also disclosed for carrying out the method according to the invention.

BRIEF DESCRIPTION OF THE DRAWINGS

The invention will be described in detail hereinafter with reference to the drawings. Therein.

DETAILED DESCRIPTION OF THE PREFERRED EMBODIMENTS

Figure 1:
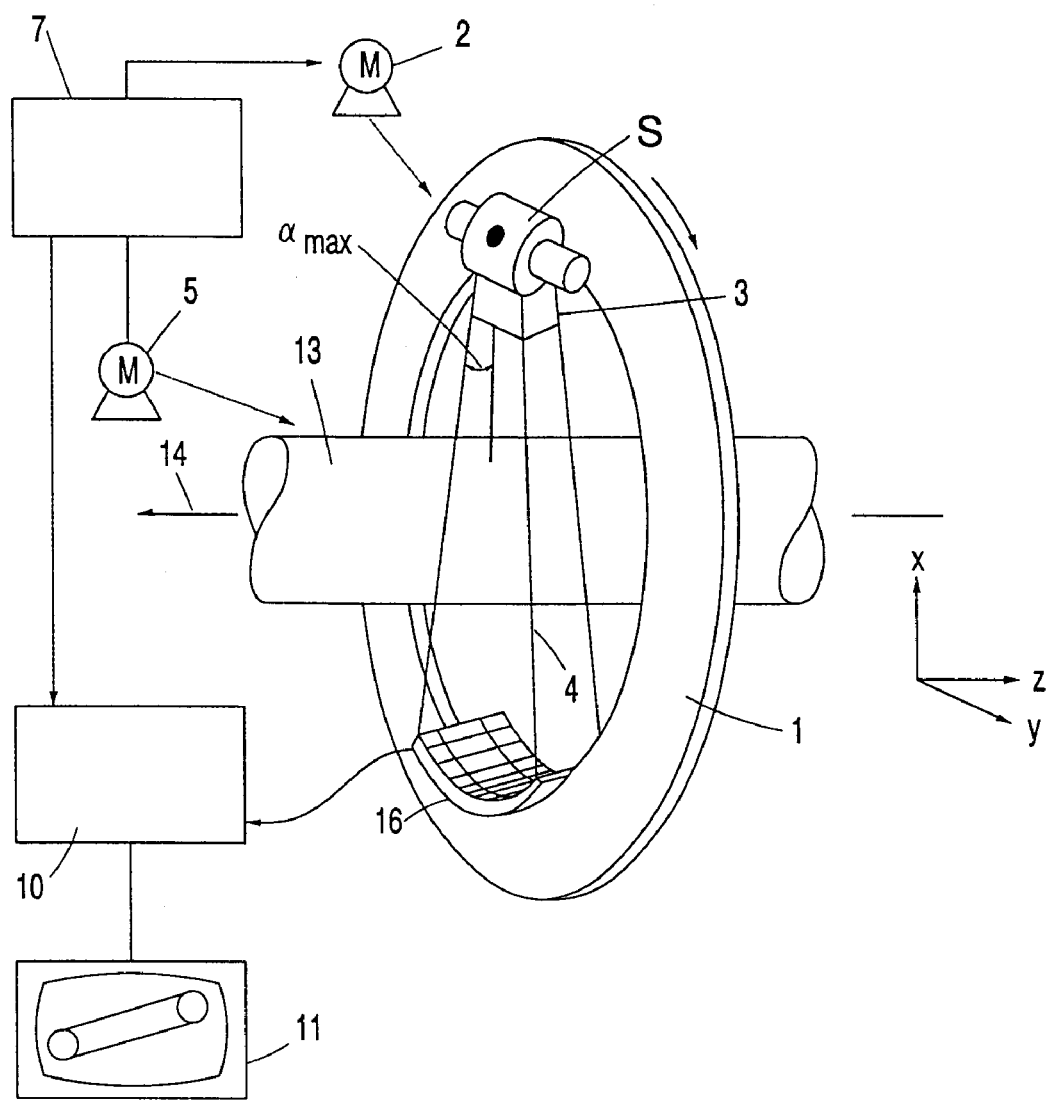
FIG. 1 shows a computed tomograph for carrying out the method according to the invention.

The computed tomograph shown in FIG. 1 includes a gantry 1 which is capable of rotation about an axis of rotation 14 which extends parallel to the z direction. To this end, the gantry 1 is driven at a preferably constant but adjustable angular speed by a motor 2. A radiation source S, for example an X-ray source, is mounted on the gantry. This source is provided with a collimator device 3 which forms a conical radiation beam 4 from the radiation produced by the radiation source S, i.e. a radiation beam having dimensions other than zero in the direction of the z axis as well as in a direction perpendicular thereto, i.e. in the x-y plane of the co-ordinate system shown in FIG. 1.

The radiation beam 4 irradiates an object (not shown) which is situated in an examination zone 13. The examination zone 13 is shaped as a cylinder which will be referred to hereinafter as the object cylinder. After having traversed the object cylinder, the X-ray beam 4 is incident on a two-dimensional detector unit 16 which is mounted on the gantry 1 and comprises a number of detector rows, each of which comprises a plurality of detector elements. In each radiation source position each detector element detects a ray of the radiation beam 4 and outputs a measured value corresponding to the intensity of this ray. The detector 16 may be arranged on an arc of circle around the axis of rotation 14, but other detector geometries are also feasible; for example, it can be mounted on an arc of circle around the radiation source S.

The angle of aperture of the radiation beam 4, denoted by the reference $\alpha_{max}$, then determines the diameter of the object cylinder 13 in which the object to be examined must be situated during the acquisition of the measured values (the angle of aperture is defined as the angle enclosed by a ray of the beam 4, situated at the edge in the x-y plane, relative to a plane defined by the radiation source S and the axis of rotation 14). The examination zone 13, or an object situated therein, for example a patient arranged on a patient table, can be displaced parallel to the direction of the axis of rotation 14 or the z axis by means of a motor 5. The speed of displacement in the z direction is preferably constant and adjustable.

The measured data acquired by the detector unit 16 are applied to an image processor 10 which reconstructs therefrom the absorption distribution in the part of the examination zone 13 which is covered by the radiation beam 4, for example, in order to display this distribution on a monitor 11. The two motors 2 and 5, the image processor 10, the radiation source S and the transfer of the measured data from the detector unit 16 to the image processor 10 are controlled by a suitable control unit 7.

When the motor 5 is stationary and the motor 2 rotates the gantry 1, there is a circular scanning motion of the X-ray source S and the detector unit 16. The control unit, however, can also control the motors 2 and 5 in such a manner that the ratio of the displacement speed of the examination zone 13 and the angular speed of the gantry is constant. In that case the radiation source S and an object present in the examination zone 13 move relative to one another along a helical path. Only this helical scanning motion will be considered hereinafter. In principle it is irrelevant whether the scanning unit 16 or the examination zone 13 performs the rotary motion or the displacement motion; only the relative motion is of importance.

Figure 2:
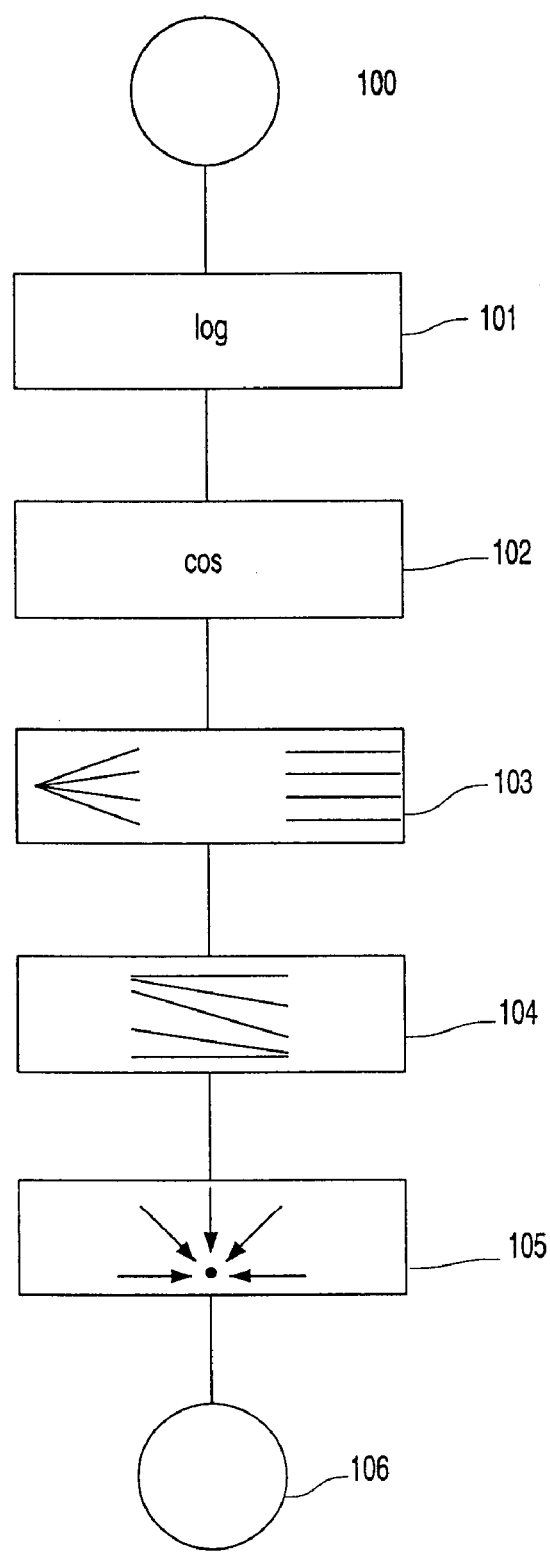
FIG. 2 shows a flow chart with the individual steps of the method.

The further processing in the image processor 10 of the signals supplied by the detector elements of the detector unit 16 during an examination will be described in detail hereinafter with reference to the flow chart shown in FIG. 2. After the initialization (block 100), the signals are acquired from the detector elements (step 101). The subsequent reconstruction of the absorption distribution exclusively utilizes signals from detector elements which are situated within a detector window (a detector window is to be understood to mean herein the part of the measuring surface which acquires exclusively the data required for the reconstruction (and no other data)). In the direction of the z axis this detector window is defined by the projection of two successive turns of the helix. It can be demonstrated that when the detector window is configured in this way, the radiation source projects each voxel in the examination zone onto the detector window from exactly 180° offset positions (in relation to the relevant voxel) upon its entry and its exit from the radiation beam.

The restriction to signals within this detector window can be achieved by shaping the detector unit accordingly. If the detector unit were shaped as an arc of circle around the axis of rotation, the development of the detector window should have the shape of a parallelogram; if the detector unit were to define (in a plane perpendicular to the axis of rotation) an arc of circle around the radiation source, a distorted parallelogram would arise. Detector units having developments of such shape are difficult to realize and not suitable for measurements during which the relative motion between the radiation source and the object to be examined is not helical but circular. However, use can also be made of a detector unit whose development is shaped as a rectangle which is so large that it encloses the development of the detector window. Using suitably shaped collimators 3, it can then be achieved that the X-rays are incident only on detector elements situated within the detector window. Instead it would also be possible to irradiate the entire measuring surface (of rectangular shape in the development) and to exclude the signals from detector elements outside the detector window from the reconstruction. If the object to be examined were a patient, however, such a patient would then be unnecessarily exposed to a higher radiation dose.

The signals from the detector elements are first digitized and divided by a reference value, the resultant quotient being logarithmated. The measured values thus produced represent the line integral of the absorption of the radiation along a ray connecting the radiation source to the relevant detector element. The subsequent processing steps then serve to determine the spatial distribution of the absorption from these line integrals.

In the step 102 the measured values are multiplied by a factor which corresponds to the cosine of the angle enclosed by the ray associated with the measured values relative to a plane perpendicular to the axis of rotation 14. This step, however, can be dispensed with in cases where the distance between two turns of the helix is small in comparison with their radius. In such cases said angle is so small that the cosine of this angle practically always has the value 1. It is also possible to reverse the order of this step and the next step.

In the step 103 a rebinning operation is performed, i.e. a step which involves the resorting and interpolation of the measured values in groups which are particularly suitable for the subsequent filtering step (block 104). This operation is based on the measured values which are produced by the real arrangement of the radiation source S with the conical radiation beam 4 and the two-dimensional detector 16 as shown in FIG. 1. Each measured value used for the reconstruction is then defined by the position of the radiation source on the helical path 17 (based on the assumption that the object to be examined is stationary while the radiation source and the detector perform the helical relative motion), as well as by the position within the detector unit 16 of the detector element having acquired this measured value.

The rebinning in the step 103 thus yields groups of measured data which would be obtained if a flat, rectangular detector in a plane containing the axis of rotation 14 were to acquire the measured data from a radiation source which extends along a helical arc 17 and emits fan beams extending perpendicularly to the detector plane and parallel to the axis of rotation 14. This is because the conical fan beam 4 can be assumed to consist of a plurality of fan beams which emanate from the relevant radiation source position and are situated in planes parallel to the axis of rotation. Corresponding sets of fan beams are obtained for other positions. The fan beams in mutually parallel planes (and the measured values associated with these fan beams) can be collected so as to form one group. This group thus contains all measured values defining the absorption of the examination zone for a given projection direction (the projection direction is defined as the direction of the rays projected onto an (x-y) plane extending perpendicularly to the axis of rotation).

Figure 3:
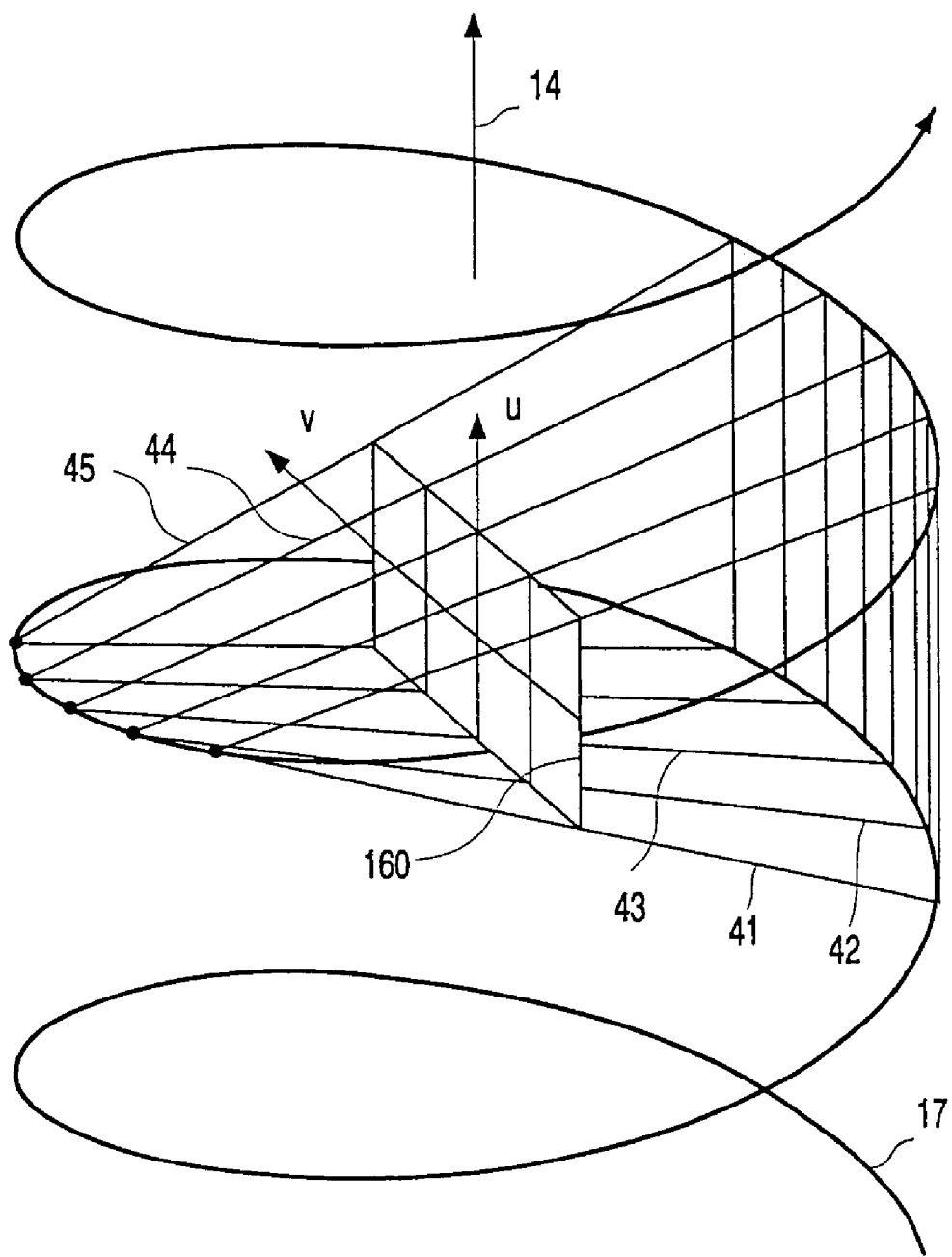
FIG. 3 illustrates the geometrical relationships underlying the rebinning.

The foregoing is illustrated in FIG. 3 which shows the fan beams 41 . . . 45 associated with a group of measured values. These fan beams are situated in parallel planes. All points of such a fan beam emanate from the helical path 17. The upper edge ray of this fan beam extends through a facing arc of the helix 17 and all lower edge rays of the fan beam extend through an arc of the helix which has been offset downwards by one turn of the helix relative to the first arc.

It can be demonstrated that the upper and the lower edge of all mutually parallel fan beams puncture a plane perpendicular to the projection direction and containing the axis of rotation 14 along two parallel horizontal lines. The two lines define, in conjunction with said plane, a virtual detector 160 and the spacing of these lines corresponds to half the distance between two neighboring turns of the helix. The rebinning operation produces measured data, possibly by interpolation, for all projection directions and for all points of an equidistant grid having the co-ordinates u,v on the virtual detector 160.

The method described thus far is known from the publication mentioned in the preamble.

This known method is supplemented by a filtering step which involves the one-dimensional filtering of those measured data which are associated with a horizontal line (extending in the v direction) of the virtual detector. The two-dimensional set of voxels, co-operating for a given projection direction during this one-dimensional filtering operation, no longer cooperates, or only partly so, for other projection directions.

The invention is based on the insight that image enhancement is achieved when each of the filtering operations in the step 104 involves each time the measured data resulting from the projection of the same voxels for the different projection directions.

Figure 4:
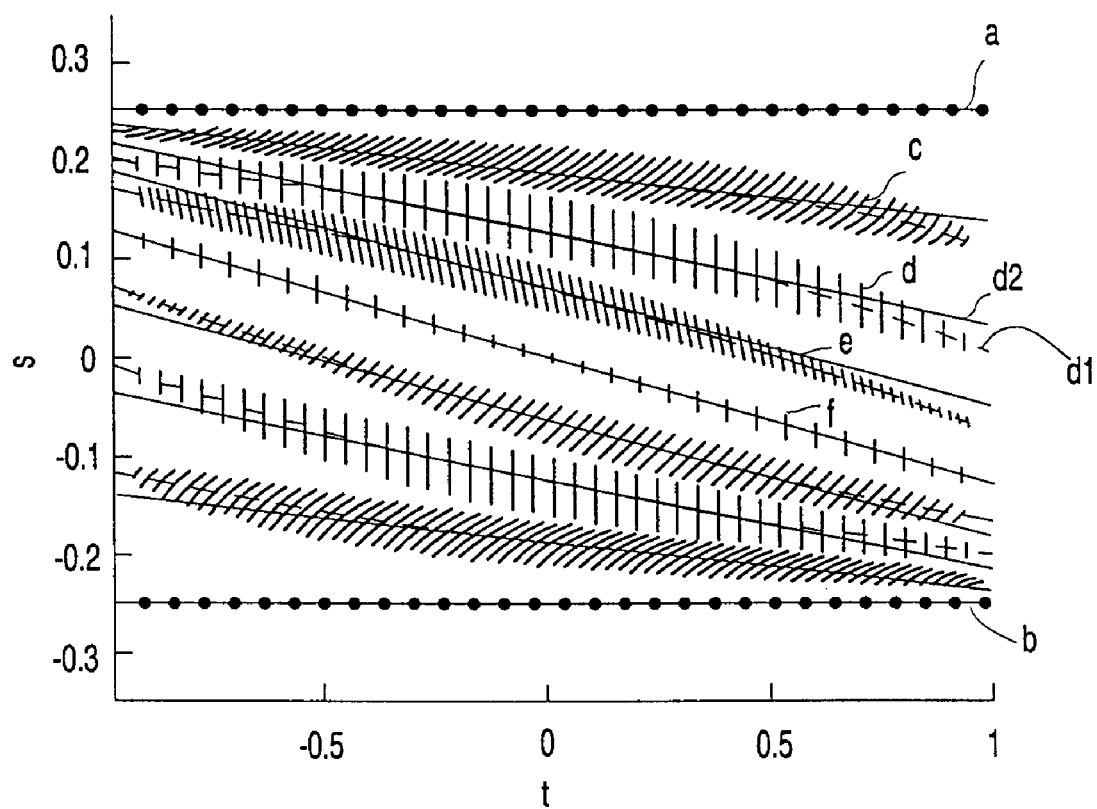
FIG. 4 shows different projections of the same voxels.

This is illustrated in FIG. 4, where s, the ordinate axis, indicates a projected deviation in a vertical direction, and t, the abscissa axis, indicates a projected deviation in a horizontal direction, relative the examination zone. FIG. 4 shows the projection of the voxels in the examination zone which are situated on the upper edge rays of the radiation beam shown in FIG. 3, i.e. for each time 22.5° offset projection directions. By definition these voxels are projected onto a horizontal straight line (a) upon entry into the fan beams 41 . . . 45, said line (a) constituting the upper edge of the detector. After a 180° change of the projection direction (during which the fan beams move one half turn of the helix upwards, together with the virtual detector 160), the same voxels in the examination zone are also projected onto a horizontal straight line (b), i.e. the lower edge of the virtual detector 160. For the projection directions situated therebetween the same voxels are no longer projected onto a straight line, but on narrow strips (c, d, e, f, etc.) which are more or less inclined relative to the horizontal straight lines a and b.

These strips overlap one another when a large number of projection directions is taken into account. Strictly speaking, therefore, it is even impossible for the filtering operations for the various projection directions to involve each time the measured data resulting from the projection of each time exactly the same voxel. However, it can thus be achieved at least approximately that the filtering takes place along a line which approximates the strips on which the voxels are projected. This line may be curved, like the dashed line d1, but also straight like the straight solid line d2.

Such a straight line is obtained as a line of intersection of a plane which approximates the surface defined by the upper edge rays of the fan beams 41 . . . 45. This plane is defined by the upper edge ray of the fan beam which extends through the axis of rotation 14 and by the upper edge of the virtual detector in the position shown in FIG. 3. The equation for such straight lines is:

$$u = m - v \frac{P}{4R\sqrt{1 + \left(1 + \frac{P}{4R}\right)^2 \tan^2\left(m\frac{2\pi}{p}\right)}} \quad (1)$$

Therein, R is the radius of the circle produced by the projection of the helix 17 onto a plane perpendicular to the axis of rotation. P is the distance between two neighboring turns of the helix, m is a parameter defined between $-P/4$ and $P/4$, u is a co-ordinate extending from the center of the virtual detector in the direction of the axis of rotation, and v is a co-ordinate on the virtual detector which is perpendicular thereto as shown in FIG. 3.

The equation (1) (and also the rendition of the various projections of the same surface on the detector 160 as shown in FIG. 4) holds only for the helical path which is shown in FIG. 3 and along which the radiation source moves counter-clockwise around the axis of rotation while moving upwards. However, if the radiation source were to rotate around the axis of rotation in the clockwise direction, the values in the equation (1) should be multiplied by the factor $-1$ (and the strips in FIG. 4 would then extend from the top left to the bottom right).

The filtering along the straight or curved line can take place in principle in that the data obtained by rebinning along these lines are subjected to convolution with a suitable one-dimensional convolution kernel. It is simpler to subject the measured data produced by the rebinning to a Fourier transformation first. The data thus transformed to the spatial frequency domain are subjected to ramp-like filtering along the line, the damping then decreasing linearly as the absolute value of the frequency increases. The data thus filtered in the spatial frequency domain are subjected to inverse Fourier transformation, thus yielding filtered measured data.

In the next step 105 a back-projection is performed on the basis of the filtered measured data. The measured data are then back-projected into the examination zone along beam paths which are the same (except for a slight modification due to the rebinning, if any) as those along which they have been acquired. The absorption values for a single voxel of the examination zone result from the superposition of all (filtered) measured data influenced by the projection of this voxel during the acquisition. For each voxel contributions are then obtained from rays in an angular range of exactly 180°. Step 106 indicates the end of processing.

What is claimed is:

1. A computed tomography method which includes the following steps:

generating, a conical radiation beam which emanates from a radiation source and traverses an examination zone or an object situated therein, generating a relative motion in the form of a helix, comprising a rotation about an axis of rotation and a displacement parallel to the axis of rotation, between the radiation source on the one side and the examination zone or the object on the other side, acquiring, during the relative motion and using a detector unit, measured values which are dependent on the intensity in the radiation beam to the other side of the examination zone, rebinning the measured values so as to form a number of groups of measured data, filtering the measured data of the groups formed by rebinning, which filtering involves filtering operations performed on different sub-groups of measured data, reconstructing the absorption in voxels of the examination zone by backprojection of the filtered measured data of different groups, characterized in that the subdivision into sub-groups is such that the measured data of different sub-groups result from different projections of voxels from at least approximately the same surface within the examination zone.

2. A computed tomography method as claimed in claim 1, characterized in that a) rebinning is such that each group contains only measured data which are associated with rays situated in planes extending parallel to one another and to the axis of rotation, b) the measured data of each group are subdivided in such a manner that those voxels which are projected onto an arc of the helix by rays of the group define the surface whose projection on the detector unit yields the measured data which form a sub-group and are subjected to a filtering operation.

3. A computed tomography method as claimed in claim 2, characterized in that the filtering operations include one-dimensional filtering of those measured data whose associated rays puncture a curved line approximating the projection of the surface on the detector unit.

4. A computed tomography method as claimed in claim 2, characterized in that each filtering operation includes one dimensional filtering of those measured data whose associated rays puncture a straight line approximating the projection of the surface.

5. A computed tomography method as claimed in claim 2, characterized in that use is made exclusively of measured data from rays which extend in the zone between two arcs of the helix which neighbor one another in the direction of the axis of rotation.

6. A computed tomography method as claimed in claim 4, characterized in that the surface is approximated by a plane, that the individual sub-groups via which a filtering operation is performed are defined by the measured data measured along a straight line present in the plane, and that the filtered measured data are used for the two-dimensional reconstruction of the absorption in the voxels of the plane.

7. A computed tomograph for carrying out the method claimed in claim 1, including a radiation source and a detector unit which is coupled thereto as well as a drive arrangement for making an object present in the examination zone and the radiation source perform a helical relative motion relative to one another, and also including a reconstruction unit for the reconstruction of the spatial distribution of the absorption within the examination zone from the measured data acquired by the detector unit, characterized in that it also includes means for rebinning the measured data into a number of groups of measured data, means for filtering the measured data of each group formed by the rebinning, which filtering involves filtering operations performed on different sub-groups of measured data, the measured data of the different sub-groups resulting from the projection of voxels from at least approximately the same surface within the examination zone.

* * * * *